(12) United States Patent
Balduf et al.

(10) Patent No.: US 8,309,668 B2
(45) Date of Patent: Nov. 13, 2012

(54) SUPERABSORBENT POLYMERS AND METHODS OF MAKING THE SAME

(75) Inventors: Torsten Balduf, Pfungstadt (DE); Günther Bub, Marl (DE); Jürgen Mosler, Castrop-Rauxel (DE); Andreas Sabbagh, Dülmen (DE); Jürgen Kohn, Rheinberg (DE); Arndt Selbach, Dirmstein (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 13/461,220

(22) Filed: May 1, 2012

(65) Prior Publication Data

US 2012/0226003 A1 Sep. 6, 2012

Related U.S. Application Data

(63) Continuation of application No. 12/063,949, filed as application No. PCT/EP2006/007973 on Aug. 11, 2006, now Pat. No. 8,178,717.

(30) Foreign Application Priority Data

Aug. 17, 2005 (DE) .......................... 10 2005 039 156

(51) Int. Cl.
C08F 220/06 (2006.01)
C08L 33/02 (2006.01)
(52) U.S. Cl. .......... 526/317.1; 526/83; 526/84; 524/556
(58) Field of Classification Search ............... 526/317.1, 526/83, 84; 524/556
See application file for complete search history.

(56) References Cited

U.S. PATENT DOCUMENTS

| | | | |
|---|---|---|---|
| 4,317,926 A | 3/1982 | Sato et al. | |
| 5,387,720 A | 2/1995 | Neher et al. | |
| 5,409,771 A | 4/1995 | Dahmen et al. | |
| 6,498,272 B1 | 12/2002 | Schroder et al. | |
| 6,664,419 B1 | 12/2003 | Bub | |
| 6,679,939 B1 | 1/2004 | Thiel et al. | |
| 6,927,268 B2 * | 8/2005 | Matsumoto et al. | 526/317.1 |
| 7,179,875 B2 * | 2/2007 | Fuchs et al. | 526/317.1 |
| 7,294,741 B2 | 11/2007 | Bub et al. | |
| 7,495,129 B2 | 2/2009 | Balduf et al. | |
| 7,557,245 B2 | 7/2009 | Nordhoff et al. | |
| 7,557,246 B2 | 7/2009 | Nordhoff et al. | |
| 7,803,969 B2 | 9/2010 | Nordhoff et al. | |
| 7,842,386 B2 * | 11/2010 | Loeker et al. | 428/407 |
| 7,939,597 B2 | 5/2011 | Bub et al. | |
| 7,964,689 B2 | 6/2011 | Nordhoff et al. | |
| 2005/0143603 A1 | 6/2005 | Bub et al. | |
| 2005/0222459 A1 | 10/2005 | Nordhoff et al. | |
| 2006/0013748 A1 | 1/2006 | Nordhoff et al. | |
| 2006/0116532 A1 | 6/2006 | Balduf et al. | |
| 2009/0023006 A1 | 1/2009 | Bub et al. | |
| 2011/0046297 A1 | 2/2011 | Hengstermann et al. | |
| 2011/0144294 A1 | 6/2011 | Bub et al. | |
| 2011/0166304 A1 | 7/2011 | Zanthoff et al. | |

FOREIGN PATENT DOCUMENTS

| | | |
|---|---|---|
| DE | 4020780 C1 | 8/1991 |
| DE | 4238493 C1 | 4/1994 |
| DE | 19904820 A1 | 8/2000 |
| DE | 10221202 A | 7/2003 |
| DE | 10201783 A1 | 8/2003 |
| DE | 10211686 A1 | 10/2003 |
| DE | 102004008574 A1 | 9/2005 |
| EP | 0887334 A1 | 12/1998 |
| EP | 1116709 A1 | 7/2001 |
| EP | 1319648 A1 | 6/2003 |
| JP | 54100315 | 8/1979 |
| JP | 61036501 B2 | 2/1986 |
| WO | 0053560 A1 | 9/2000 |
| WO | 2004063134 A1 | 7/2004 |

OTHER PUBLICATIONS

English translation of the International Preliminary Report on Patentability completed on Jun. 24, 2008 in PCT/EP2006/007973.
International Search Report mailed on Jan. 30, 2007 in PCT/EP2006/007973.
International Preliminary Report on Patentability completed on Nov. 26, 2007 in PCT/EP2006/007973.

* cited by examiner

*Primary Examiner* — Michael M Bernshteyn
(74) *Attorney, Agent, or Firm* — Smith Moore Leatherwood LLP; Philip P. McCann

(57) ABSTRACT

The present invention relates to a process for producing a superabsorbent a polymer comprises (I) producing a pure (meth)acrylic acid comprising the steps of (a) synthesizing a crude (meth)acrylic acid phase; (b) distillatively working-up the crude (meth)acrylic acid phase to obtain a (meth)acrylic acid phase and a dimer phase comprising (meth)acrylic acid dimers or (meth)acrylic acid oligomers or both; (c) splitting at least a part of the (meth)acrylic acid dimers or of the (meth) acrylic acid oligomers or both from the dimer phase to obtain a (meth)acrylic acid-comprising low boiling phase and a high boiling phase comprising less (meth)acrylic acid than the low boiling phase; (d) separating at least a part of the (meth) acrylic acid from the low boiling phase to obtain a pure (meth)acrylic acid, and a residue; (II) polymerizing a monomer phase comprising the pure (meth)acrylic acid to obtain a polymer phase; and (III) working-up the polymer phase to obtain the polymer.

11 Claims, 1 Drawing Sheet

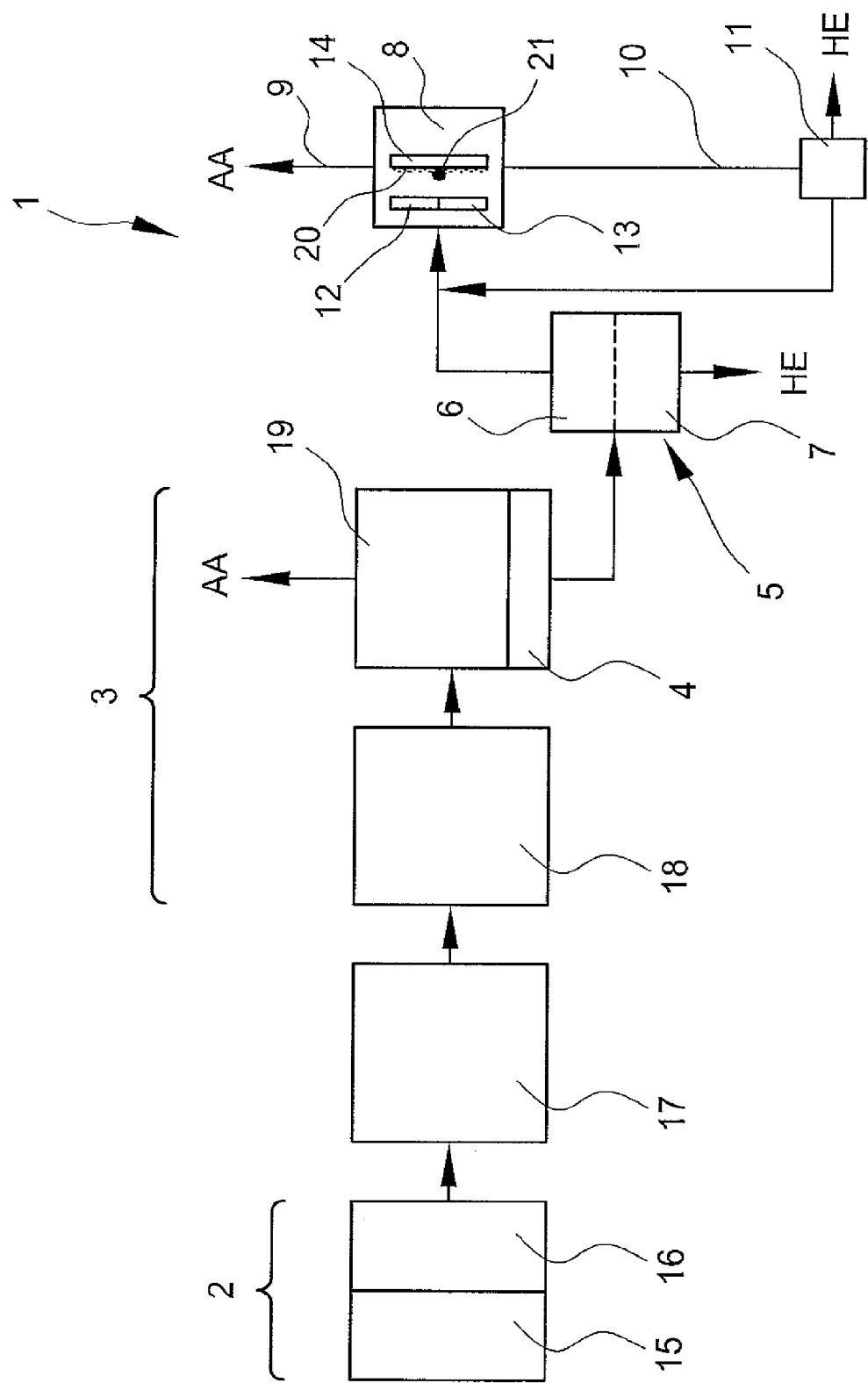

SUPERABSORBENT POLYMERS AND METHODS OF MAKING THE SAME

This application is a continuation application of U.S. application Ser. No. 12/063,949 filed 30 Jul. 2008, now U.S. Pat. No. 8,178,717, which is a national stage application under 35 U.S.C. 371 of international application No. PCT/EP2006/007973 filed 11 Aug. 2006, and claims priority to German Application No. DE 10 2005 039 156.7 filed 17 Aug. 2005, the disclosures of which are expressly incorporated herein by reference.

Aspects of embodiments and embodiments of the present invention relate to a process for production of (meth)acrylic acid, a device for production of (meth)acrylic acid, a process for production of a polymer as well as chemical products based on or comprising (meth)acrylic acid or a polymer as well as the use of (meth)acrylic acid or polymers in chemical products.

BACKGROUND

"(Meth)acrylic acid" is used in this text for the compounds with the nomenclature names "methacrylic acid" and/or "acrylic acid". Of the two compounds, acrylic acid is the subject of aspects of embodiments according to the present invention.

(Meth)acrylic acid can be produced by various processes. Of particular interest are processes that start from petrochemical products such as propylene. In this context, the propylene can be converted on the one hand by catalytic gas phase oxidation or also by vapor phase oxidation with an oxygen-containing gas such as air, first to acrolein and then to acrylic acid. In this way, in a two-step process, the propylene is first oxidized catalytically to acrolein, which is then converted to acrylic acid in a second process step, likewise using catalysts. The thus-obtained acrylic acid is removed from the gaseous reaction mixture by absorption with water to form an aqueous solution or with high-boiling solvents to form a high-boiling solution. The purification of the acrylic acid then generally occurs by azeotropic distillation of the acrylic acid solution, followed by further purification steps. In a comparable way the synthesis of methacrylic acid by catalytic oxidation of isobutylene, t-butanol, methacrolein or isobutyl aldehyde can occur in a gas phase.

Also, there have been attempts to carry out the catalytic reaction in solution rather than in the gas phase. This can occur on the one hand with homogeneous catalysts and on the other hand with heterogeneous catalysts, such as are known, for example, from DE 102 01 783 A1. Another way of producing acrylic acid starts first with a polyol such as glycerine, which is dehydrated to acrolein, as described in DE 42 38 493 C1. The thus-obtained acrolein can then be converted either by gas phase oxidation or by solution oxidation respectively in the presence of heterogeneous catalysts or homogeneous catalysts to acrylic acid.

It is common for the (meth)acrylic acid present in the products of these various acrylic acid or methacrylic acid production processes to have insufficient purity to be used directly for further processing into polymers or other subsequent products. In particular in connection with the production of superabsorbers, which are based substantially upon lightly cross-linked partially neutralized polyacrylic acid and are more closely described in F. L. Buchholz and A. T. Graham in "Modern Superabsorbent Technology", Wiley-VCH, New York, 1998. In the case of the production of superabsorbers, which are mostly used in hygiene articles such as diapers, incontinence products and feminine hygiene articles or medical products such as wound dressings, particularly high demands are made on the purity of the (meth)acrylic acid. This makes it necessary for the products of the above described (meth)acrylic acid production processes to be subjected to one or more purification steps. In the industrial production of (meth)acrylic acid, these purification steps are generally one or more distillations. Although distillation as a purification method is well established on the industrial scale and has long proven itself, in distillative purification, dimers or oligomers often form because of the heating of the (meth)acrylic acid associated therewith.

In order to convert these (meth)acrylic acid dimers and/or oligomers into the respective monomer, the prior art makes a number of suggestions.

Thus, for example, JP Sho 61-36501 B2 describes a thermal splitting of the dimeric acrylic acid with a simultaneous distillation of the split monomeric acrylic acid. This leads to a separation of a large part of the high boiling components, but leaves the concentration of maleic acid, maleic acid anhydride and protoanemonin, which can form at the same time as impurities in addition to the (meth)acrylic acid dimers and/or oligomers, almost unchanged. The thus-worked-up flow is fed back to the process for production of (meth)acrylic acid and effects an enrichment of protoanemonin, maleic acid and maleic acid anhydride in the fine purified acrylic acid, which reduces its quality and is particularly disadvantageous with respect to a further processing of this acrylic acid in radical polymerization, since these impurities favor chain breaking reactions and chain transfer reactions in radical polymerization.

Furthermore, EP 0 887 334 A1 describes the process for recycling acrylic acid from a composition comprising acrylic acid dimers, acrylic acid, and maleic acid, whereby first the acrylic acid is separated in a distillation device, and the bottom product obtained in the distillation, which is enriched with the acrylic acid dimers and with the acrylic acid, is converted in a dimer splitting reactor. Finally, the bottom product obtained in the dimer splitting reactor is conducted back into the distillation device. A reduction of the concentration of protoanemonin is not mentioned, although protoanemonin is a hindrance in the further processing of the acrylic acid. Furthermore, the arrangement described in EP 0 887 334 A1 with a subsequently connected dimer splitting reactor and with partial recycling of the head stream of the dimer splitting reactor into the pre-connected distillation device leads to an unnecessary increase of the supply flow into the distillation device and thereby necessitates a larger size of the distillation device.

Aspects of embodiments and embodiments of the present invention relate to at least partially alleviating or to completely overcoming the disadvantages arising from the state of the art.

Further aspects of embodiments and embodiments of the present invention relate to economically working-up the impurities that are present in crude (meth)acrylic acid, such as dimers and/or oligomers and also maleic acid, maleic acid anhydride or protoanemonin, during its purification.

Furthermore, aspects of embodiments and embodiments of the present invention relate to achieving a conversion of the (meth)acrylic acid dimers and/or oligomers into (meth)acrylic acid while at the same reducing enrichment of further impurities such as, for example, maleic acid, maleic acid anhydride or protoanemonin.

Further aspects of embodiments and embodiments of the present invention relate to providing a device for generation of high purity (meth)acrylic acid, which achieves a purification of impure (meth)acrylic acid to highest purity with low energy expenditure, with as few operational disruptions as possible and more environmentally friendly operation and with as low a loss as possible of (meth)acrylic acid in the form of dimeric (meth)acrylic acid or trimeric (meth)acrylic acid or higher oligomers.

In addition, aspects of embodiments and embodiments of the present invention relate to a process and a device, whereby the risk of uncontrolled polymerization of (meth)acrylic acid during the production and in particular during the purification of (meth)acrylic acid is reduced.

In addition, aspects of embodiments and embodiments of the present invention relate to improving, by suitable process improvements and device improvements, the production of (meth)acrylic acid in such a way that the production of chemical products that use polymers of (meth)acrylic acid or that are based upon (meth)acrylic acid is improved.

Numerous other aspects of embodiments, embodiments, features, and advantages of the present invention will appear from the description and the accompanying drawings. In the description and/or the accompanying drawings, reference is made to exemplary aspects of embodiments and/or embodiments of the invention, which can be applied individually or combined in any way with each other. Such aspects of embodiments and/or embodiments do not represent the full scope of the invention. Reference should therefore be made to the claims herein for interpreting the full scope of the invention.

A process according to aspects of embodiments and embodiments of the present invention for production (meth)acrylic acid comprises the steps of:

a) synthesizing of a crude (meth)acrylic acid phase;
b) distillatively working-up the crude (meth)acrylic acid phase to obtain:
   a (meth)acrylic acid phase, and
   a dimer phase comprising (meth)acrylic acid dimers or (meth)acrylic acid oligomers or (meth)acrylic acid dimers and (meth)acrylic acid oligomers;
c) splitting at least a part of the (meth)acrylic acid dimers or of the (meth)acrylic acid oligomers or (meth)acrylic acid dimers and (meth)acrylic acid oligomers from the dimer phase to obtain:
   a (meth)acrylic acid-comprising low-boiling phase, and
   a high-boiling phase comprising less (meth)acrylic acid than the low-boiling phase;
d) separating at least a part of the (meth)acrylic acid from the low-boiling phase by forming of one or more crystals to obtain:
   a pure (meth)acrylic acid and
   a residue.

The crude (meth)acrylic acid phase comprises (meth)acrylic acid in one aspect of an embodiment a range from about 1 to about 80 wt. %, in another aspect a range from about 5 to about 75 wt. % and in yet another aspect a range from about 7 to about 70 wt. %, respectively based on the crude (meth)acrylic acid phase. The other components of the crude (meth)acrylic acid phase can on the one hand be carriers such as solvents, for example water or aromatics having boiling points higher than (meth)acrylic acid or carrier gases or at least two of the above components. Furthermore, the crude (meth)acrylic acid phase often comprises impurities such as dimers or oligomers of (meth)acrylic acid, aldehydes, for example acid acetaldehyde, furfural or benzaldehyde, propionic acid, acetic acid, maleic acid, maleic acid anhydride or protoanemonin. The aldehyde content in one aspect of an embodiment often lies in a range from about 100 to about 2,000 ppm and in another aspect in a range from about 200 to about 1,000 ppm. The maleic acid and maleic acid anhydride contents lie in one aspect of an embodiment in a range from about 500 to about 5,000 ppm and in another aspect in a range from about 1,000 to about 2,000 ppm. The dimers or oligomers content lie in one aspect of an embodiment in a range from about 0.01 to about 2 wt. % and in another aspect in a range from about 0.2 to about 0.6 wt. %. The acetic acid content lies in one aspect of an embodiment in a range from about 0.2 to about 10 wt. % and in another aspect in a range from about 2 to about 4 wt. %. The water content lies in one aspect of an embodiment in a range from about 10 to about 50 wt. % and in another aspect in a range from about 30 to about 40 wt. %. The propionic acid content lies in one aspect of an embodiment less than about 0.1 wt. % and in another aspect less than about 0.05 wt. %. The protoanemonin content lies in one aspect of an embodiment in a range from about 10 to about 1,000 ppm and in another aspect in a range from about 100 to about 200 ppm. As noted, the above contents can be applied individually or combined in any way with each other. The weight amounts (in ppm or in wt. %) are respectively based upon the total weight of the crude (meth)acrylic acid phase.

In aspects of an embodiment relating to a process according to the present invention, the synthesis according to step a) is selected from the group consisting of (i.) gas phase oxidation, (ii.) dehydration of an organic molecule comprising at least one OH-group, optionally in one aspect followed by an oxidation and in another aspect the optional oxidation comprises gas phase oxidation, (iii.) a liquid phase oxidation.

The synthesis path of the gas phase oxidation is generally known to a skilled person and disclosed, among others, in EP 1 319 648 A1. For dehydration, in addition to glycerine, a hydroxycarboxylic acid such as lactic acid or β-hydroxypropionic acid are suitable as organic molecule comprising at least one OH-group.

If glycerine is used as such a molecule, acrolein forms in the dehydration reaction, which can subsequently be subjected to an oxidation, in one aspect either a gas phase oxidation or a liquid phase oxidation and in another aspect a gas phase oxidation, to obtain acrylic acid. For the case of β-hydroxypropionic acid, acrylic acid is obtained directly by dehydration. Suitable dehydration conditions are known to the skilled person and can be found, among others, in DE 42 38 493 C1. Routes for liquid phase oxidation for the production of (meth)acrylic acid are also known to the skilled person and can also be found in, for example, DE 102 01 783 A1.

In further aspects of an embodiment relating to the process according to the present invention, the distillative work-up according to step b) occurs in at least two distillation steps following each other. To this end, the mostly liquid crude (meth)acrylic acid phase—generally coming from an absorption or quench column—is fed into the first distillation column for carrying out the first distillation step and, after carrying out the first distillation step, the (meth)acrylic acid-richer phase is subjected to a further distillation step. In general, aspects include the distillative work-up occurring in two, three or four distillation steps, whereby one aspect includes three distillation steps between the absorption and/or quench step and the splitting step c). The (meth)acrylic acid phase obtained from the distillative work-up of the crude (meth)acrylic acid in one aspect comprises at least about 90 wt. %, in another aspect a range from about 92 to about 99.9 wt. % and yet another aspect a range from about 95 to about 99.8 wt. % (meth)acrylic acid, respectively based upon the (meth)acrylic acid phase. The dimeric phase which likewise forms during the distillative work-up of the crude (meth)acrylic acid phase is preferably based upon:

(α1) in one aspect about 0.1 to about 75 wt. %, another aspect about 5 to about 70 wt. %, and yet another aspect about 10 to about 65 wt. % monomeric (meth)acrylic acid;

(α2) in one aspect about 1 to about 90 wt. %, another aspect about 10 to about 40 wt. %, and yet another aspect about 20 to about 30 wt. % (meth)acrylic acid dimers;

(α3) in one aspect about 1 to about 25 wt. %, another aspect about 2 to about 20 wt. %, and yet another aspect about 5 to about 15 wt. % (meth)acrylic acid trimers;

(α4) in one aspect 0 to about 20 wt. %, another aspect about 1 to about 10 wt. %, and yet another aspect about 2 to about 8 wt. % water;

(α5) in one aspect about 1 to about 92 wt. %, another aspect about 10 to about 75 wt. %, and yet another aspect about 40 to about 57 wt. % oligomers which are larger than (meth) acrylic acid trimers; and/or (α6) in one aspect about 1 to about 20 wt. %, another aspect about 2 to about 15 wt. %, and yet another aspect about 5 to about 10 wt. % further compounds which are different from the α1-, α2-, α3-, α4- and α5-compounds, as side products, in particular maleic acid anhydride, whereby the sum of the components (α1) to (α6) is 100 wt. %.

In further aspects of an embodiment relating to the process according to the present invention, the splitting according to step c) occurs thermally. To this end, in one aspect suitable temperatures range from about 50 to about 500° C., in another aspect from about 150 to about 400° C., and in yet another aspect from about 250 to about 300° C. It has further proven advantageous to carry out the splitting in one aspect at a pressure ranging from about 0.1 to about 1,000 bar, in another aspect from about 10 to about 800 bar, and in yet another aspect from about 80 to about 600 bar. Accordingly, in one aspect relating to a process according to the present invention, the splitting according to step c) occurs at a pressure which is different from about the ambient pressure. The ambient pressure is here the pressure which is found at the location of the splitting device due to the respective climatic conditions. The residence of the dimer phase during the splitting in a suitable splitting area in one aspect ranges from about 0.1 to about 1 hour, in another aspect from about 1 second to about 15 minutes and in yet another aspect from about 1 minute to about 10 minutes.

According to aspects of an embodiment relating to a process according to the present invention, the splitting occurs in the presence of a splitting agent, which in one aspect comprises water. The water and the (meth)acrylic dimers or (meth)acrylic oligomers are used in a weight ratio water:(meth)acrylic acid dimers and/or (meth)acrylic acid oligomers in one aspect ranging from about 0.01:1 to about 10:1, in another aspect from about 0.1:1 to about 8:1, and in yet another aspect from about 0.5:1 to about 6:1.

In particular aspects of an embodiment relating to the process according to the present invention, the water is used in one aspect in a molar amount which is at most about 90%, in another aspect at most about 80%, and in yet another aspect at most about 50% of the molar amount of (meth)acrylic acid which is bound in dimeric or oligomeric form (two (meth)acrylic acid molecules in a dimer, three (meth)acrylic acid molecules in a trimer, etc.).

In further particular aspects of an embodiment relating to the process according to the present invention, the water is used in one aspect in a molar amount which is at least about 50%, in another aspect at least about 80%, and in yet another aspect at least about 90% of the molar amount of the (meth)acrylic acid, which is bound in dimeric or oligomeric form.

In general, the skilled person will determine the amount of water as splitting agent that is appropriate for splitting simply by suitable prior experiments. Thus the skilled person will continue to add water, at the selected pressure and temperature conditions, until as complete a splitting as possible has occurred and/or until also with further addition of water, no further formation of monomeric (meth)acrylic acid can be observed.

In aspects of an embodiment relating to the production and working-up of acrylic acid, the low-boiling phase formed in the splitting comprises acrylic acid dimers and acrylic acid trimers in one aspect in a total amount ranging from 0 to about 10 wt. %, in another aspect from about 0.1 to about 5 wt. %, and in yet another aspect from about 0.5 to about 1 wt. %, respectively, based on the weight of the low-boiling phase.

The high-boiling phase comprises in one aspect at least about 5 wt. %, in another aspect at least about 10 wt. %, and in yet another aspect about 20 wt. % (meth)acrylic acid less than the low-boiling phase.

In further aspects of an embodiment relating to the process according to the present invention, at least a part of the low-boiling phase in step d) is conducted as fluid film over a cold source. In this context, in one aspect the cold source has a surface temperature ranging from about −40 to about 5° C., in another aspect from about −20 to about 0° C., and in yet another aspect from about −10 to about −1° C. The conduction of the fluid film over the cold source is in an aspect understood to be such that the cold source comprises a surface that comes into contact with the fluid film during its conduction thereover. In a further aspect the fluid film on the one hand is conducted over the cold source by gravity. In addition, it corresponds to aspects of an embodiment of the present invention in which the fluid film is conducted over the cold source by the action of a pump. In a further aspect it is possible for the fluid film to be conducted over a cold source both by means of gravity as well as by pump action. In a particular aspect of an embodiment relating to the process according to the present invention, the fluid film is moved by means of gravity. In yet another particular aspect of an embodiment relating to the process according to the present invention, at least a part of the fluid film is present as falling film.

A cold source includes in principal all cold-generating devices, which appear to the skilled person to be suitable for the aspects of embodiments of the present invention. Thus, in an aspect the cold source can be present in gaseous form, in which a cold gas flow is blown through the fluid film or the fluid film is conducted through a cold gas flow. In, however, another aspect of an embodiment according to the present invention, the cold source is designed with a solid surface. In a further aspect of an embodiment according to the present invention, the cold source is formed at least partially planar. In this way, the fluid film can come into contact with the at least partially formed area of the cold source to facilitate transfer of the cold of the cold source to the fluid film (e.g., heat is removed from the fluid film through contact with the at least partially formed area of the cold source). This measure also makes it possible that one or more crystals from at least one component of the fluid film can form on the surface of the cold source. In one aspect of an embodiment according to the present invention, a crystal layer forms in this way at least partially over areas on the surface of the cold source, in turn over which the fluid film can flow.

In further aspects of an embodiment relating to the process according to the present invention, at least a part of the crystals is subjected to a sweating. In one aspect, this sweating is generally achieved by slowly increasing the temperature of the crystals slightly. In another aspect, this temperature increase occurs slightly above the crystallization point or melting point of the crystals. The crystallization point or melting point of the crystals is in yet another aspect increased by at least about 1° C., in still yet another aspect about 2 to about 20° C., and in yet still yet another aspect by about 1.5 to about 5° C.

In general, during the sweating process, care is taken that the crystals caused to sweat do not fully melt, but rather at most only to a small amount. In one aspect, this amount is at most about 20 wt. %, in another aspect at most about 10 wt. %, and in yet another aspect at most about 5 wt. % of the crystal amount before the start of the sweating.

In further aspects of an embodiment relating to the process according to the present invention, the crystals are melted after the sweating. In one aspect, the melting occurs, in comparison to the sweating, at a higher temperature than the sweating temperature. In another aspect, the melting temperature lies at least about 1° C., in yet another aspect at least about 5° C., and in still yet another aspect at least about 10° C. above the sweating temperature. The temperature measurements can be made at the boundary surface between cold source and crystals. In connection with the purification of acrylic acid, in one aspect the melting temperature ranges from about 15 to about 50° C. and in another aspect from about 30 to about 40° C.

In further aspects of an embodiment relating to the process according to the present invention, the residue from step d) is at least partially separated by a further crystallization in step e) into
a (meth)acrylic acid-rich phase and
an impurity phase.

In the context of the further crystallization, in aspects of embodiments relating to the process according to the present invention, the (meth)acrylic acid-rich phase is at least partially conducted into the process step d). By this measure, a clear improvement of the input factor can be achieved.

The device according to aspects of embodiments relating to the present invention for production of (meth)acrylic acid comprises, connected with each other in a fluid-conducting fashion:
α a synthesis area;
β downstream of the synthesis area, a distillative work-up area, comprising a bottom zone formed in a lower region of the work-up area;
γ downstream of the bottom zone, a heatable pressure container comprising an upper region and a lower region; and/or
δ downstream of the upper region, a crystallization area comprising a first outlet and at least one further outlet.

A fluid conducting fashion means, according to aspects of embodiments of the present invention, that the individual device components and/or units are connected together in such a way that liquids, gases and/or solids can be transported between individual components and/or units. In one aspect, this transport between individual components and/or units occurs by means of liquid-conducting pipe work systems or gas-conducting pipe work systems.

A synthesis area is designed, according to the requirements of the respective synthesis parts, to be carried out in a way that is familiar to the skilled person. In one aspect relating to the case of the gas phase oxidation, the synthesis area comprises two reactors connected with each other, which comprise a solid state catalyst, which is present either as powder or as layer or as a combination thereof, in one aspect on plates or in another aspect in pipes, which in yet another aspect are arranged in bundles. In the case of the dehydration of glycerine, two reactors connected with each other are likewise present. The first is formed as dehydration reactor in the form of a pressure container. The second reactor for conversion of acrolein to acrylic acid is likewise designed, as already described for the gas phase oxidation. For the dehydration of β-hydroxypropionic acid to acrylic acid, only one reactor is necessary.

The distillative work-up area is in one aspect designed as one or more distillation columns, which is in another aspect connected, particularly in the case of gas phase oxidation, to a quench and/or absorption area.

The splitting area is also characterized as dimers splitter and is made from pressure resistant materials known to the skilled person, such as stainless steel. It is, in particular, designed in such a way that it can be operated at pressures of at least about 10 bar and temperatures of at least about 200° C. The splitting area is, additionally, in one aspect corrosion resistant.

In the context of the crystallization area, in one aspect this comprises an at least partially planar cooling unit. This cooling unit can consist of one, two or more elements. In another aspect according to an embodiment, the cooling unit is formed from pipes, whereby the product to be cooled flows through these pipes on the inside, and in the outer area, a cooling agent or heating agent flows around the pipes. In another aspect, the planar cooling units are present as plates, which can also be arranged in plate series. These plates can in turn comprise hollow spaces. On the one hand, the product to be cooled can flow through these hollow spaces. In this case, the plates would be brought to the respectively suitable temperature by means of a cooling medium or heating medium that passes by the outer surfaces of these plates. In another form, the product to be cooled could be conducted past the outer surfaces of the plates, whereby the cooling agent or heating agent flows through the openings in the plates.

In a further aspect according an embodiment relating to the present invention, the crystallization area comprises an at least partially planar heating unit. In an additional aspect according to the present invention, the crystallization area comprises at least one partially planar cooling unit. In a further aspect according to another embodiment of the present invention, the crystallization area comprises an at least partially planar heating/cooling unit. By the provision of a heating/cooling unit in the crystallization area, it is possible to follow a crystal formation at the heating/cooling unit with a sweating and melting process. In, therefore, a particular aspect according to the present invention relating to the crystallization area, the heating/cooling unit is formed at the same location. This can occur, for example, by means of a pipe, which accommodates the product to be cooled on its inside and which can be flowed around on the outside either by a heating agent or by a cooling agent. In this way, at one and the same pipe section, both a cooling for crystal formation as well as a heating process for sweating or melting can occur. In a particular aspect relating to the crystallization areas according to the present invention, the installation parts helpful for the operation are commercially obtainable from the Company Sulzer Chemtech AG, Switzerland.

In a further aspect of an embodiment relating to a device according to the present invention, the device further comprises
ε downstream of the at least one further outlet, a further crystallization unit.

Any crystallization unit that appears suitable to the skilled person can be used, including commercially obtainable crystallization units such as, among others, those from Sulzer Chemtech AG or also those from Niro Process Technology BV, Netherlands. In an aspect, the crystallization area operates dynamically, i.e., continuously, while the crystallization unit operates statically—also characterized as "batchwise".

In a further aspect of an embodiment relating to the process according to the present invention, a device according aspects of embodiments and embodiments relating to the present invention is used. The process according to aspects of an embodiment of the present invention for the production of a polymer comprises the steps of:

I. producing pure (meth)acrylic acid according to a process according to aspects of embodiments and/or embodiments the present invention;
II. polymerizing of a monomer phase comprising the pure (meth)acrylic acid to obtain a polymer phase,
III. working-up of the polymer phase to obtain a polymer.

The polymer according to aspects of an embodiment of the present invention is a superabsorber, in this case it is recommended that the acrylic acid monomer is at least partially neutralized with a base, in one aspect sodium hydroxide and that cross-linker is present during the polymerization. Further details concerning the production of a superabsorber can also be found, in addition to the above-mentioned reference from Buchholz, in DE 40 20 780 C1. It is, furthermore, not absolutely necessary for the polymerization process according to aspects of an embodiment of the present invention to only use the pure (meth)acrylic acid from the process according to aspects of embodiments and/or embodiments of the present invention. The work-up of the polymer phase can occur by precipitation in a precipitation solvent that does not dissolve the polymer formed, by drying or by distillation of the solvent used in the polymerization according to methods familiar to the skilled person.

Furthermore, aspects of embodiments and/or embodiments of the present invention relate to fibers, sheets, formed articles, food or feed additives, pharmaceuticals, cosmetics, foams, superabsorbers, hygiene articles, paper, leather or textile additives, comprising or based upon a (meth)acrylic acid obtainable according to a process according to the invention or comprising or based on a polymer obtainable according to a polymerization process according to aspects of embodiments and/or embodiments of the present invention.

In addition, aspects of embodiments and/or embodiments of the present invention relate to a use of a (meth)acrylic acid obtainable according to a process according to aspects of embodiments and/or embodiments of the present invention or of a polymer obtainable according to a polymerization process according to aspects of embodiments and/or embodiments of the present invention in or for fibers, sheets, formed articles, food or feed additives, pharmaceuticals, cosmetics, foams, superabsorber, hygiene articles, paper additives, leather additives or textile additives.

In this context, the use of the (meth)acrylic acid, in particular acrylic acid, produced according to the process according to aspects of embodiments and/or embodiments of the present invention, in the production of superabsorbing polymers (superabsorbers) is highlighted. In an aspect, superabsorbers are used in hygiene articles such as diapers, incontinence products and feminine hygiene articles. Here, the superabsorber is incorporated according to processes generally known to the skilled person into absorbent members, also known as cores. These cores are, in turn, arranged between a liquid permeable top sheet and a generally liquid impermeable bottom sheet of the hygiene articles.

Furthermore, aspects of embodiments and/or embodiments of the present invention are illustrated by way of example by non-limiting figures.

FIG. 1 shows a schematic representation of the device according to aspects of embodiments and/or embodiments of the invention.

In FIG. 1, a production device 1 comprises a synthesis area 2, which comprises, for example in the case of the production of acrylic acid an acrolein reactor 15 for the gas phase oxidation of propene and an acrylic acid reactor 16 for the gas phase oxidation of acrolein. A quench unit 17 is connected at the acrylic acid reactor 16. The crude acrylic acid formed therein is transferred from there into a work-up area 3 with a first column 18 followed by a second column 19. At a bottom area 4 in the further column 19 is connected a pressure container 5 functioning as "dimer splitter". Purified acrylic acid (AA) leaves the further column 19 via its head. At an upper region 6 of the pressure container 5, a crystallization area 8 is connected. Impurities (HE in FIG. 1) forming during the splitting are discarded from a lower region 7 of the pressure container 5. Via a first outlet 9, the purified acrylic acid (AA) obtained in crystallization area 8 is discharged. At a further outlet 10 of the crystallization area 8, a crystallization unit 11 is connected, out of which impurities (HE) are discarded and an acrylic acid-rich phase is conducted back to the crystallization area 8. The crystallization area 8 comprises a cooling unit 12, a heating unit 13 and a heating/cooling unit 14, over which a falling film 20 is conducted, out of which crystals 21 can form by cooling, which are first caused to sweat by heating and can than be melted.

LIST OF REFERENCE NUMERALS 1 production device
2 synthesis area
3 work-up area
4 bottom area
5 pressure container
6 upper region
7 lower region
8 crystallization area
9 first outlet
10 further outlet
11 crystallization unit
12 cooling unit
13 heating unit
14 heating/cooling unit
15 acrolein reactor
16 acrylic acid reactor
17 quench unit
18 first column
19 further column
20 falling film
21 crystal

The invention claimed is:
1. A process for producing a superabsorbent polymer comprising the steps of:
I a) producing crude (meth)acrylic acid phase wherein crude (meth)acrylic acid comprises from about 1 to about 80 wt % of (meth)acrylic acid; wherein said producing crude (meth)acrylic acid phase is selected from the group consisting of gas phase oxidation, dehydration of an organic molecule having at least one OH-group wherein the organic molecule is selected from the group consisting of glycerine, lactic acid and β-hydroxypropionic acid, optionally followed by an oxidation, and liquid phase oxidation;

b) distilling the (meth)acrylic acid phase of a) to obtain a (meth)acrylic acid phase, and a dimer base comprising (meth)acrylic acid dimers or (meth)acrylic acid oligomers or both;

c) splitting at least a part of the (meth)acrylic acid dimers or of the (meth)acrylic acid oligomers or both from the dimer phase to obtain a (meth)acrylic acid-comprising low boiling phase, and a high boiling phase comprising less (meth)acrylic acid than the low boiling phase, wherein said high boiling phase is discarded;

d) separating at least a part of the (meth)acrylic acid from the low boiling phase by forming one or more crystals to obtain a pure (meth)acrylic acid and a residue;

II. polymerizing the (meth)acrylic acid in the presence of a cross linker to obtain a superabsorber polymer phase; and III. working-up the polymer phase to obtain the superabsorbent polymer.

2. The process according to claim 1, wherein at least a part of the low boiler phase in step d) is provided as fluid film over a cold source.

3. The process according to claim 2, wherein at least a part of the fluid film comprises a falling film.

4. The process according to claim 2, wherein the cold source comprises an at least partially planar form.

5. The process according to claim 1, wherein at least a part of the crystals are subjected to a sweating.

6. The process according to claim 5, wherein the crystals are melted after the sweating.

7. The process according to claim 1, wherein the distillative work-up according to step b) occurs in at least two distillation steps following each other.

8. The process according to claim 1, wherein the splitting according to step c) occurs thermally.

9. The process according to claim 8, wherein the splitting according to step c) occurs under a pressure which is different from the ambient pressure.

10. The process according to claim 1, further comprising the step of e) crystallizing the residue of step d) into a (meth) acrylic acid-rich phase, and an impurity phase.

11. The process according to claim 10 wherein the (meth) acrylic acid-rich phase is at least partially supplied to process step d).

* * * * *